United States Patent [19]

Green

[11] Patent Number: 4,610,250
[45] Date of Patent: Sep. 9, 1986

[54] TWO-PART SURGICAL FASTENER FOR FASCIA WOUND APPROXIMATION

[75] Inventor: David T. Green, Norwalk, Conn.

[73] Assignee: United States Surgical Corporation, Norwalk, Conn.

[21] Appl. No.: 785,501

[22] Filed: Oct. 8, 1985

[51] Int. Cl.4 .................. A61B 17/04; A61B 17/08
[52] U.S. Cl. .................. 128/334 C; 128/337; 128/335; 411/450; 411/469
[58] Field of Search .............. 411/450, 469; 24/625, 24/35, 36, 93-95; 128/334 C, 335, 337

[56] References Cited

U.S. PATENT DOCUMENTS

| | | | |
|---|---|---|---|
| 816,026 | 3/1906 | Meier . | |
| 2,684,070 | 7/1954 | Kelsey | 128/337 |
| 3,098,232 | 7/1963 | Brown | 1/349 |
| 3,150,379 | 9/1964 | Brown | 1/349 |
| 3,166,072 | 1/1965 | Sullivan, Jr. | 128/334 |
| 3,203,220 | 8/1965 | Kaepernik | 72/410 |
| 3,209,754 | 10/1965 | Brown | 128/337 |
| 3,234,636 | 2/1966 | Brown | 29/212 |
| 3,258,012 | 6/1966 | Nakayama et al. | 128/334 |
| 3,273,562 | 9/1966 | Brown | 128/337 |
| 3,283,557 | 11/1966 | Wood | 72/386 |
| 3,357,296 | 12/1967 | Lefever | 85/49 |
| 3,534,352 | 8/1985 | Korthoff | 128/334 C |
| 3,595,201 | 7/1971 | Oudenhoven | 116/114 |
| 3,598,299 | 8/1971 | Johnson | 227/144 |
| 3,641,804 | 2/1972 | Oudenhoven | 72/409 |
| 3,744,495 | 7/1973 | Johnson | 128/337 |
| 3,812,859 | 5/1974 | Murphy et al. | 128/330 |
| 3,879,783 | 4/1975 | Giulie | 11/1 R |
| 3,899,914 | 8/1975 | Akiyama | 72/410 |
| 3,924,629 | 12/1975 | Akiyama | 128/325 |
| 3,926,193 | 12/1975 | Hasson | 128/335 |
| 4,006,747 | 2/1977 | Kronenthal et al. | 128/335 |
| 4,060,089 | 11/1977 | Noiles | 128/325 |
| 4,127,227 | 11/1978 | Green | 227/83 |
| 4,278,091 | 7/1981 | Borzone | 128/334 C |
| 4,402,445 | 9/1983 | Green | 227/19 |
| 4,489,875 | 12/1984 | Crawford et al. | 227/19 |
| 4,506,671 | 3/1985 | Green | 128/334 R |
| 4,513,746 | 4/1985 | Aranyi et al. | 128/334 C |
| 4,523,591 | 6/1985 | Kaplan et al. | 128/334 R |
| 4,532,927 | 8/1985 | Miksza, Jr. | 128/334 C |
| 4,535,772 | 8/1985 | Sheehan | 128/337 |

FOREIGN PATENT DOCUMENTS

| | | |
|---|---|---|
| 932998 | 9/1973 | Canada . |
| 0129442 | 12/1984 | European Pat. Off. . |
| WO83/1190 | 4/1983 | PCT Int'l Appl. . |
| 972731 | 10/1964 | United Kingdom . |

Primary Examiner—Richard C. Pinkham
Assistant Examiner—Gary Jackson
Attorney, Agent, or Firm—Thomas R. Bremer

[57] ABSTRACT

A two-art surgical fastener is provided for joining and approximating the edges of a wound in body tissue such as fascia tissue. The fastener, which can be made of an absorbable resinous material, has a fastener member and a retainer member. The fastener member has four prongs which mate with four openings in the retaining member. The two end prongs are tension legs, holding the fastener together. The two inner prongs are bent toward each other by camming surfaces in the corresponding openings in the retainer, approximating the edges of the wound.

13 Claims, 5 Drawing Figures

TWO-PART SURGICAL FASTENER FOR FASCIA WOUND APPROXIMATION

BACKGROUND OF THE INVENTION

This invention relates to surgical fasteners, and more particularly to a two-part fastener for facilitating the approximation of the edges of a wound or incision in body tissue, particularly fascia tissue.

Surgical stapling devices allow a surgeon to fasten body tissue by applying surgical fasteners, such as staples or clips. The fasteners may be applied singly in succession or a number may be applied simultaneously. Surgical fasteners are often made of metals such as tantalum or stainless steel, which are inert. Fasteners of magnesium, which fasteners are gradually absorbed by the body, are also known.

Non-metallic fasteners are also known and in some cases may have certain advantages over metal fasteners. For example, metal fasteners in the body may scatter X-rays and may therefore degrade the quality of radiographs.

However, metal fasteners also have certain advantages over non-metallic fasteners. They can be bent or crimped and will hold their new shape in or around tissue. In contrast, objects of non-metallic resinous materials are usually too resilient (i.e., elastic) to hold deformed shapes (assuming plastic flow does not occur). (As used herein, the term "resinous materials" means non-metallic materials, such as natural or synthetic polymers and resins, including protein-based materials, which are relatively flexible and elastic, and which may or may not be absorbable in the body.)

To circumvent this characteristic of resinous materials, surgical fasteners of these materials may be made in two parts: a fastener member and a retainer member. The prong or prongs of the fastener member are driven through one side of the tissue to be fastened and the retainer member interlocks with the prongs of the fastener member on the other side of the tissue to hold the entire fastener structure in place. One such fastener structure and apparatus for applying it are disclosed in Green U.S. Pat. No. 4,402,445, issued Sept. 6, 1983, which is hereby incorporated by reference as background material not essential to the practice of this invention.

However, two-part fasteners of the type described in the above-incorporated patent have heretofore been unable to perform the function of uniting two edges of a wound or incision in fascia tissue and maintain the edges in sufficiently close approximation for healing to occur properly. That function has been better served by metallic staples or clips which could be applied partly on each edge of the wound or incision (hereinafter "wound") and then clinched to force the edges together and maintain the edges in close approximation.

It would be advantageous to be able to provide a fastener of resinous material, particularly absorbable resinous material, capable of joining the edges of sub-wounds in body tissue, particularly fascia tissue, and maintaining the edges of the wound in close approximation.

SUMMARY OF THE INVENTION

It is an object of this invention to provide a fastener of resinous material, particularly absorbable resinous material, capable of joining the edges of wounds in body tissue, particularly fascia tissue, and maintaining the edges of the wound in close approximation.

It is a further object of this invention to provide a method of joining and approximating the edges of wounds in body tissue, particularly fascia tissue.

In accordance with the present invention, there is provided a surgical fastener for joining and approximating the edges of a wound in body tissue. The fastener comprises a fastener member and a retainer member. The fastener member has an elongated base and at least four substantially parallel prongs extending substantially perpendicularly from the base in substantially the same direction. A first prong is adjacent one end of the base and a second prong is adjacent the other end of the base. The remaining prongs are spaced inwardly of the first and second prongs. The retainer member is approximately equal in length to the base and has a plurality of openings corresponding to the number of prongs for engaging the prongs and interlocking the fastener and retainer members. The openings corresponding to two adjaent ones of the remaining prongs have internal camming surfaces for deforming the two adjacent prongs when the fastener is applied to close a wound in body tissue and those two prongs are applied on opposing sides of the wound, such that the two prongs bend toward one another, thereby approximating the edges of the wound.

A method of applying the fastener is also provided.

BRIEF DESCRIPTION OF THE DRAWINGS

The above and other objects and advantages of the invention will be apparent after consideration of the following detailed description, taken in conjunction with the accompanying drawings, in which like reference characters refer to like parts throughout, and in which.

DETAILED DESCRIPTION OF THE INVENTION

Figure 1:
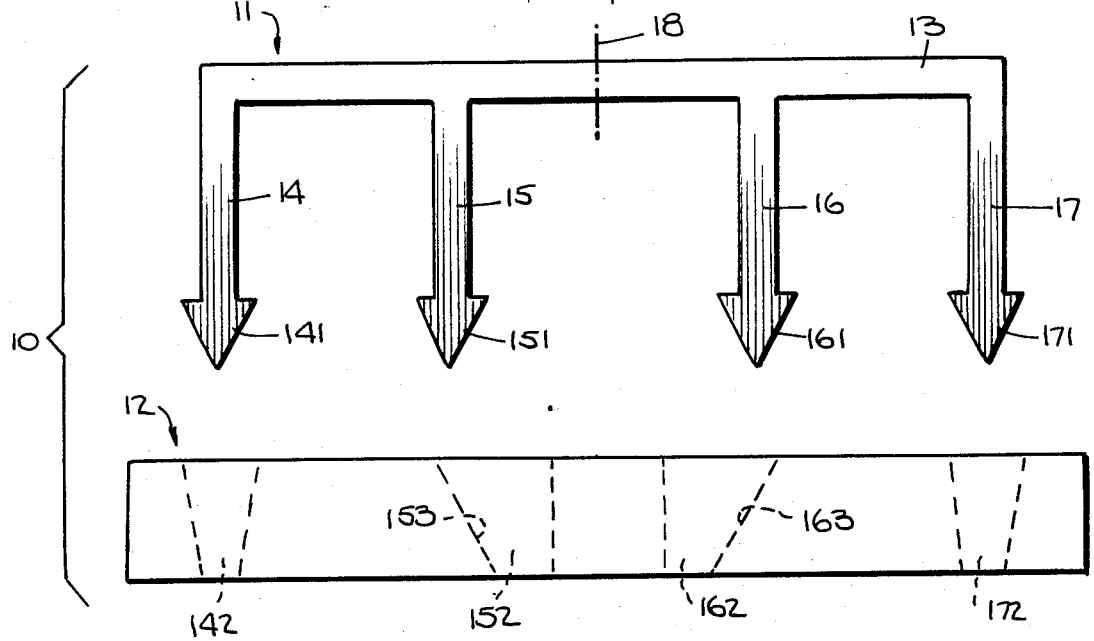
FIG. 1 is an elevational view of a surgical fastener according to the present invention.

A preferred embodiment 10 of a fastener according to the present invention is shown in FIG. 1. As shown, fastener 10 has a fastener member 11 and a retainer member 12. Both members may be made from a resinous material which may or may not be absorbable in the body. A preferred absorbable material is disclosed in commonly-assigned Kaplan et al. U.S. Pat. No. 4,523,591, hereby incorporated by reference as background material not essential to the practice of this invention.

Fastener member 11 has a base 13 and most preferably has four substantially parallel prongs 14–17 extending substantially perpendicularly from base 13 in substantially the same direction. Fastener member 11 could have more than four prongs although it preferably has an even number of prongs. The prongs 14–17 preferably are symmetrically spaced about transverse centerline 18 of base 13. Each prong 14–17 has a barb 141, 151, 161, 171 on the end thereof remote from the base. Retainer member 12 is approximately equal in length to, but slightly longer than, base 13, and has four openings 142, 152, 162, 172 for mating with prongs 14–17 and barbs 141, 151, 161, 171 to interlock the fastener and retainer members 11, 12. Openings 142, 172 adjacent ends of retainer member 12 correspond to prongs 14, 17 adjacent the ends of base 13. The two remaining openings 152, 162, spaced inwardly from the ends of retainer member 12, correspond to the two adjacent remaining prongs 15, 16, spaced inwardly from the ends of base 13. Openings 152, 162 have internal camming surfaces 153, 163, for purposes which will be discussed in more detail below.

Figure 2:
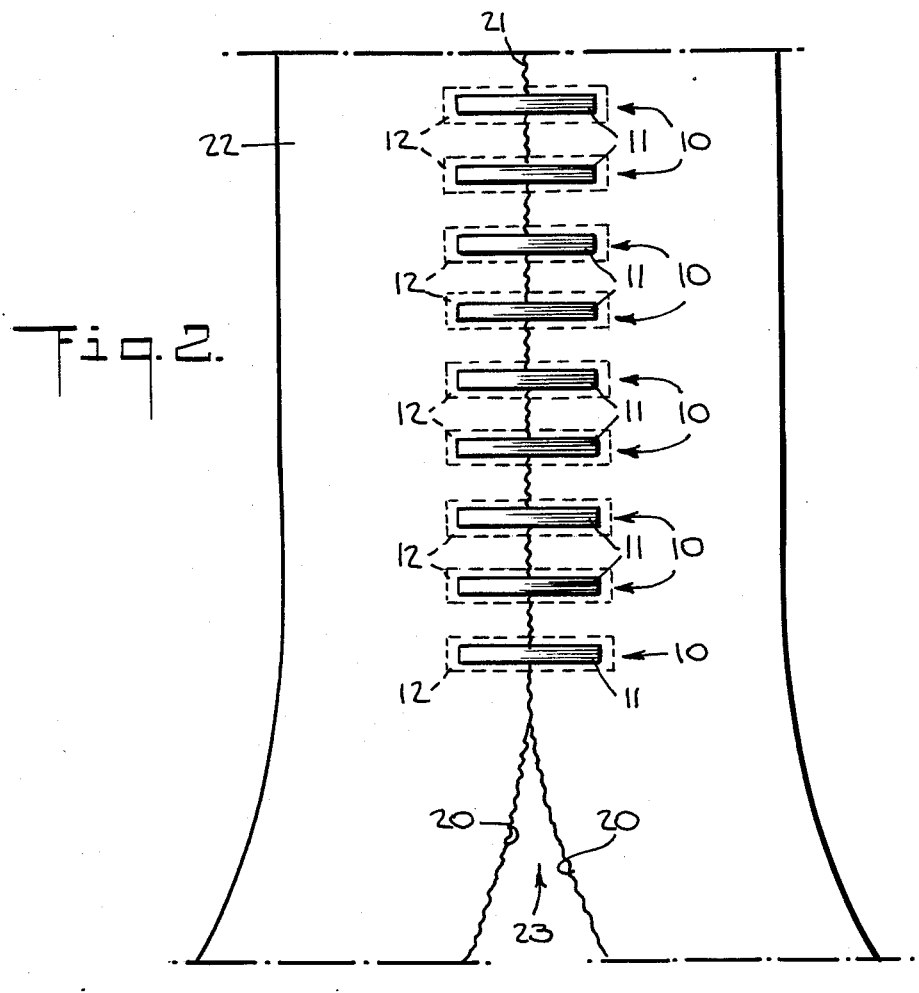
FIG. 2 is a plan view of a wound closed by surgical fasteners according to the invention.

FIG. 2 shows how edges 20 of wound 21 in tissue 22 can be joined and approximated by a row of fasteners 10 of the present invention.

Figure 3:
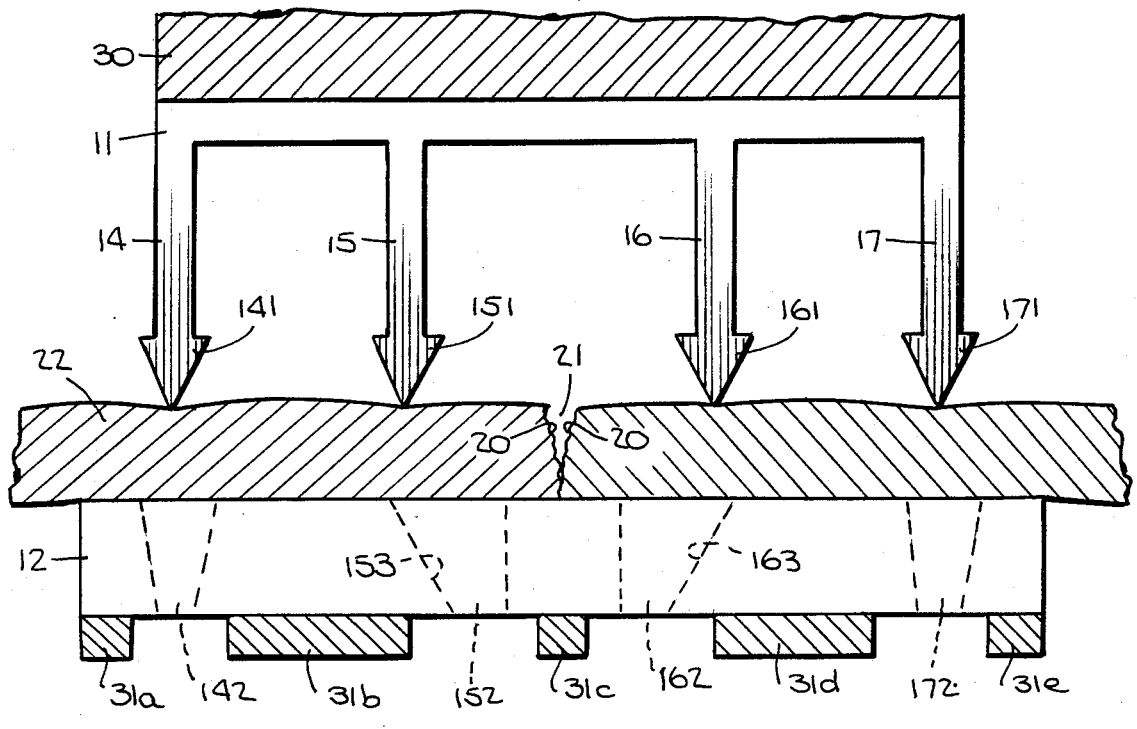
FIGS. 3-5 are sequential, partially fragmentary, cross-sectional views of a fastener according to the invention being applied to body tissue by fastener-applying apparatus.
Figure 4:
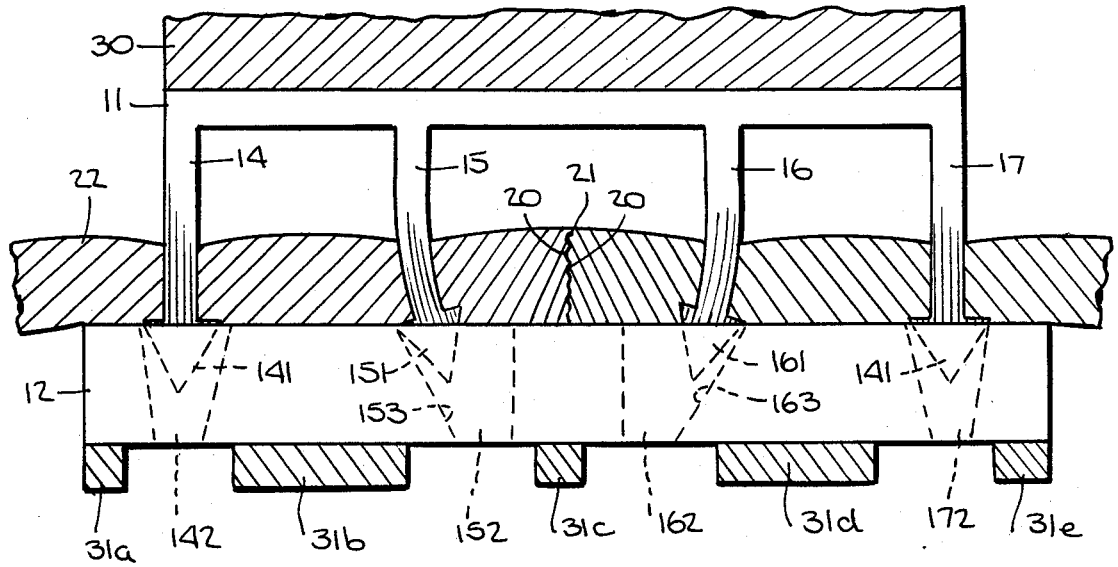
Figure 5:
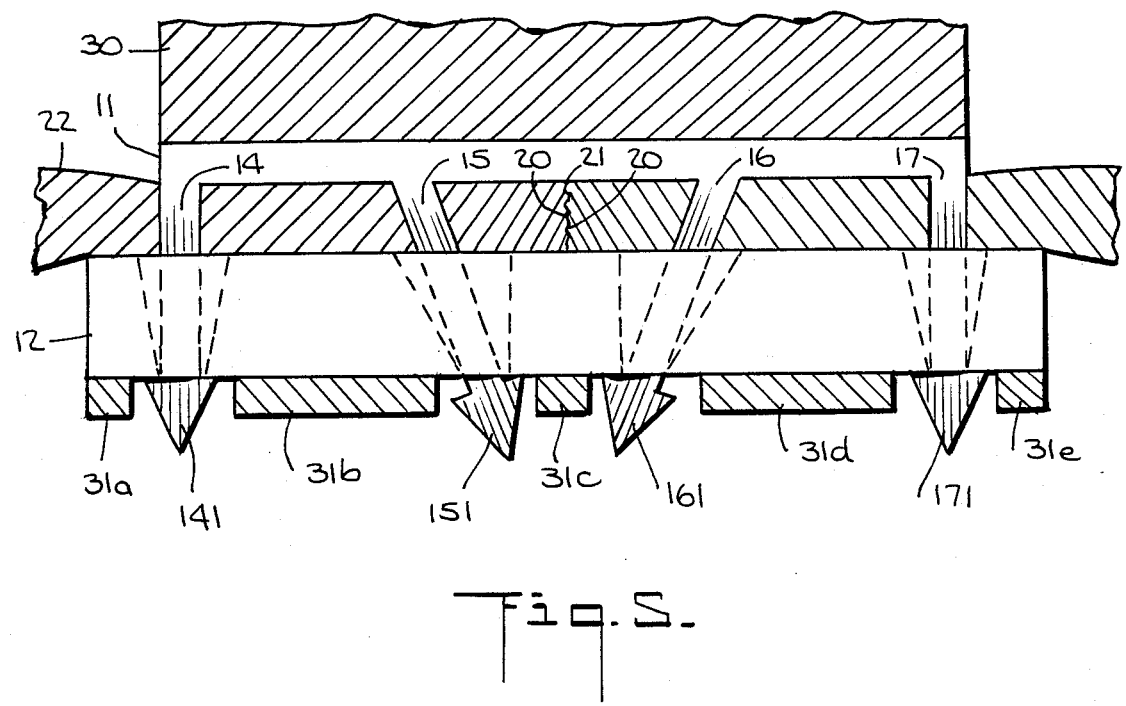

FIGS. 3–5 show the sequence by which fastener 10 is applied to wound 21. Fastener 10 is applied by apparatus adapted for that purpose. The apparatus has a pusher member 30 for pushing fastener member 11 through tissue 22, and an anvil portion which holds retainer member 12 on the other side of tissue 22 including anvil members 31a–e for holding retainer member 12 and tissue 22 against the force exerted by pusher member 30.

In the view shown in FIG. 3, the apparatus has been placed on either side of tissue 22 and both fastener member 11 and retainer member 12 are in contact with the tissue. Members 11, 12 have been placed so that adjacent inward prongs 15, 16 are approximately centered about wound 21, which has been brought together, but whose edges 20 are not well approximated.

In the view shown in FIG. 4, sufficient pressure has been applied to pusher member 30 to force prongs 14–17 through tissue 22 and partially through openings 142, 152, 162, 172. Barbs 151, 161 have contacted camming surfaces 153, 163 and, as a result, prongs 15, 16 have begun to bend toward each other, moving edges 20 of wound 21 with them. As can be seen, wound 21 has closed completely with edges 20 well approximated.

As shown in FIG. 5, the insertion of fastener 10 is complete with prongs 15, 16 fully deformed and bringing edges 20 of wound 21 toward one another. All prongs 14–17 are completely through openings 142, 152, 162, 172 and barbs 141, 151, 161, 171 maintain the engagement of fastener member 11 and retainer member 12.

To apply the fasteners, the anvil portion of the fastener-applying apparatus is inserted through the wound itself—e.g., through space 23 in FIG. 2. After a row of fasteners 10 has been applied and the apparatus removed, a small portion of the wound will remain and will have to be closed by known techniques.

As seen in the completed fastener 10 of FIG. 5, prongs 14, 17 serve as tension legs, holding the fastener together, while prongs 15, 16 serve as tissue-approximating legs. As discussed above, a fastener according to this invention can have more than four prongs. Such a fastener member might be used in very tough tissue where it is necessary to have more than two tension legs. Preferably, there is always an even number of prongs symmetrically spaced about transverse centerline 18 of base 13, so that the fastener can be easily centered about the wound. If there is an odd number of prongs, the center of the fastener would have to be offset from the wound for the tissue-approximating prongs to be positioned on either side of the wound.

Thus, a surgical fastener of resinous material is provided which is capable of joining and approximating the edges of wounds in body tissue. Those skilled in the art will appreciate that the present invention can be practiced by other than the embodiments described, which are presented for purposes of illustration and not of limitation, and the present invention is limited only by the claims which follow.

What is claimed is:

1. A surgical fastener for joining and approximating the edges of a wound in body tissue, said fastener comprising:
   a fastener member including:
   an elongated base, and
   at least four substantially parallel prongs extending substantially perpendicularly from the base in substantially the same direction, a first one of said prongs being adjacent one end of said base, a second one of said prongs being adjacent the other end of said base, and the remainder of said prongs being spaced inwardly from said first and second prongs; and
   a retainer member having a length approximately equal to the length of said base and having a plurality of openings therein corresponding to the number of said prongs for engaging said prongs and interlocking said fastener and retainer members, the openings corresponding to two adjacent ones of said remainder of said prongs having internal camming surfaces for deforming said two adjacent prongs when said fastener is applied to close a wound in body tissue and said two adjacent ones of said remainder of said prongs are applied on opposite sides of said wound, such that said two adjacent prongs bend toward one another, thereby approximating the edges of said wound.

2. The fastener of claim 1 wherein said fastener member and said retainer member are made of resinous material.

3. The fastener of claim 2 wherein said resinous material is absorbable in the body.

4. The fastener of claim 1 wherein said prongs are symmetrically spaced about the transverse centerline of said base.

5. The fastener of claim 4 comprising an even number of said prongs, said two adjacent ones of said prongs being substantially equidistant from the transverse centerline of said base.

6. The fastener of claim 5 wherein said even number is four.

7. In combination:
   apparatus for applying at least one surgical fastener to join and approximate the edges of a wound in body tissue, each of said fasteners having a fastener member and a retainer member;
   at least one fastener member positioned within the apparatus, said fastener member including an elongated base and at least four substantialy parallel prongs extending substantially perpendicularly from said base in substantially the same direction, a first one of said prongs being adjacent one end of said base, a second one of said prongs being adjacent the other end of said base, and the remainder of said prongs being spaced inwardly from said first and second prongs; and
   a corresponding number of retainer members positioned within the apparatus, each of said retainer members having a length approximately equal to the length of said base and having a plurality of openings therein corresponding to the number of said prongs for engaging said prongs and interlocking said fastener and retainer members, the openings corresponding to two adjacent ones of said remainder of said prongs having internal camming surfaces for deforming said two adjacent prongs when said fastener is applied to close a wound in body tissue and said two adjacent ones of said remainder of said prongs are applied on opposite sides of said wound, such that said two adjacent prongs bend toward one another, thereby approximating the edges of said wound.

8. The combination of claim 7 wherein said fastener members and said retainer members are made of resinous material.

9. The combination of claim 8 wherein said resinous material is absorbable in the body.

10. The combination of claim 7 wherein said prongs are symmetrically spaced about the transverse centerline of said base.

11. The combination of claim 10 comprising an even number of said prongs, said two adjacent ones of said prongs being substantially equidistant from the transverse centerline of said base.

12. The combination of claim 11 wherein said even number is four.

13. A method of joining and approximating the edges of a wound in body tissue, said method comprising the steps of:

providing a surgical fastener comprising:

a fastener member including an elongated base and at least four substantially parallel prongs extending substantially perpendicularly from said base in substantially the same direction, a first one of said prongs being adjacent one end of said base, a second one of said prongs being adjacent the other end of said base, and the remainder of said prongs being spaced inwardly from said first and second prongs, and a retainer member having a length approximately equal to the length of said base and having a plurality of openings therein corresponding to the number of said prongs for engaging said prongs and interlocking said fastener and retainer members, the openings corresponding to two adjacent ones of said remainder of said prongs having internal camming surfaces;

providing apparatus for applying said fastener:

positioning said apparatus such that said each of said two adjacent ones of said prongs overlies one of said edges of said wound; and applying said fastener to said wound, such that said two adjacent prongs are deformed by said camming surfaces such that they bend toward one another, thereby approximating the edges of said wound.

* * * * *